US00PP14555P39

(12) United States Plant Patent
Carruth

(10) Patent No.: US PP14,555 P3
(45) Date of Patent: Feb. 24, 2004

(54) MINIATURE ROSE PLANT NAMED 'WEKYEGI'

(50) Latin Name: *Rosa hybrida*
Varietal Denomination: Wekyegi

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 31 days.

(21) Appl. No.: 10/075,805

(22) Filed: Oct. 25, 2001

(65) Prior Publication Data

US 2003/0084488 P1 May 1, 2003

(51) Int. Cl.[7] ..... A01H 5/00
(52) U.S. Cl. ..... Plt./125
(58) Field of Search ..... Plt./111, 118, 125

*Primary Examiner*—Howard J. Locker
(74) *Attorney, Agent, or Firm*—Christie, Parker & Hale, LLP

(57) ABSTRACT

A new variety of Miniature Rose suitable for garden decoration, having flowers of Lemon Yellow coloration.

1 Drawing Sheet

BACKGROUND OF THE INVENTION

This invention relates to a new and distinct variety of Miniature Rose (*Rosa hybrida*). The varietal denomination of the new variety is 'WEKYEGI'. It has as its seed parent the variety known as 'POUlxas' (U.S. Plant Pat. No. 9,420) and as its pollen parent an un-disseminated seedling of my creation.

SUMMARY OF THE INVENTION

Among the features which distinguish the new variety from other presently available and commercial rose cultivars known to the inventor are the following combination of characteristics: its moderately smooth stems with few prickles, its lasting Yellow coloration, its very double petalage and its bright Green foliage. The new variety has a miniature bushy, upright and compact growing habit, suitable for outdoor garden decoration.

Asexual reproduction of the new variety by budding as performed in Kern County and Upland, Calif., shows that the foregoing and other distinguishing characteristics come true to form and are established and transmitted through succeeding propagation. 'WEKYEGI' may be asexually propagated by cuttings, budding and grafting.

COMPARISON WITH PARENTS

The new variety may be distinguished from its seed parent, 'POUlxas' by the following combination of characteristics: whereas 'WEKYEGI' bears somewhat large flowers (about 5.2 to 6.0 cm in diameter) of Lemonade Yellow coloration, 'POUlxas' bears significantly smaller flowers (about 3.5 to 5.0 cm in diameter) of Apricot Orange coloration.

The new variety may be distinguished from its pollen parent, an un-disseminated seedling of my creation by the following combination of characteristics: whereas 'WEKYEGI' bears very double (about 52 to 72 petals) flowers of Lemonade Yellow coloration, the pollen parent bears semi-double (about 15 to 22 petals) flowers of blended Orange coloration. The new variety bears Bright Green foliage whereas the pollen parent bears significantly Darker Green foliage.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Royal Horticultural Society Colour Chart (1966) and terminology used in the color descriptions herein refers to plate numbers in this color chart except where common terms of color definition are employed.

DESCRIPTION OF THE NEW VARIETY

The following description is of 3 to 4 year-old plants of the new variety grown outdoors in Upland, Calif. in the month of September. Phenotypic expression may vary with environmental, cultural and climatic conditions, as well as differences in conditions of light and soil.

FLOWER

The new variety sometimes bears its flowers singly, usually in clusters of 3 or more per stem. Flowers are borne in irregular rounded clusters on average strong short to medium stems (about 11 to 20 cm). Outdoors, the plant blooms very abundantly and nearly continuously during the growing season. The flowers have a slight fragrance.

BUD

The peduncle is about 3.3 to 4.9 cm in length, of average caliper (about 0.15 to 0.3 cm in diameter), and usually erect. It is almost entirely smooth, with some stipitate glands. Peduncle color is between 144A and 138B.

Before the calyx breaks, the bud is pointed to ovoid in shape and about 0.8 to 1.4 cm in diameter at the widest point, about 1.4 to 1.9 cm in length.

The surface of the bud bears some foliaceous appendages, numerous hairs and some stipitate glands, usually with slender foliaceous parts extending beyond the tip of the bud about ¼ or more of its length.

Bud color is between 144A and 138B.

The sepals are about 1.9 to 2.6 cm in length and about 0.4 to 0.7 cm in width at the widest point.

The outer surface of the sepal is between 144A and 138B. The inner surface of the sepal is between 148C and 139D and covered with fine wooly tomentum.

Sepal margins are lined with some stipitate glands and hairs.

As the petals open (after the calyx breaks), the bud is about 1.0 to 1.5 cm in diameter at the widest point, about 1.6 to 2.1 cm in length, and pointed to ovoid in form.

The color of the under surfaces of the newly opened petals is between 14C and 16C. The color of the upper surfaces of the newly opened petals is between 12B and 15C. There is no visible change in coloration at the point where the petal attaches.

BLOOM

When fully open, the bloom ranges from about 5.2 to 6.0 cm in diameter. Petalage is very double with about 52 to 72 petals and numerous petaloids arranged irregularly.

When partially open, the bloom form is somewhat cupped, and the petals are loosely spiraled to cupped with petal edges slightly reflexed outward.

When fully open, the bloom form is very cupped and full to flat, and the petals are more loosely cupped to flat with petal edges moderately reflexed outward.

PETALS

The substance of the petals is somewhat heavy and of medium thickness, with upper surfaces slightly shiny and under surfaces more satiny.

The outer petals are nearly round to broadly ovate in shape with rounded apices. The inner petals are more narrowly obovate to broadly lanceolate in shape with rounded apices.

The petals are about 1.1 to 2.1 cm in length and about 0.6 to 2.1 cm in width at the widest point.

Petal margins are entire.

NEWLY OPENED FLOWER

The under surface of the outer, intermediate and inner petals is between 4C and 16C. The upper surface of the outer petals is between 12B and 15C. There is no visible change in coloration at the point where the petal attaches.

The general tonality of the newly opened flower is between 12B and 15C.

THREE-DAY-OLD FLOWER

The under and upper surface of the outer and inner petals is between 12C and 15D. There is no visible change in coloration at the point where the petal attaches.

The general tonality of the three-day-old flower is between 12C and 15D.

On the spent bloom, the petals usually persist, fading to between 9D and 14D.

In September in Upland, Calif., blooms on the bush growing outdoors generally last about 4 to 5 or more days. Cut roses from plants grown outdoors and kept at normal indoor living temperatures generally last about 4 to 5 or more days.

MALE REPRODUCTIVE ORGANS

Stamens are few in number (average about 22) and are arranged regularly about the pistils; a few are mixed with petaloids or tucked in the calyx.

The filaments are of very short length (about 0.2 to 0.4 cm), some without anthers. Filaments are between 3C and 14B in color.

The anthers are small to medium for the class and all open approximately at the same time. Anther color is near 17D when immature and near 167D at maturity.

Pollen is very sparse.

FEMALE REPRODUCTIVE ORGANS

Pistils vary in number (average about 20).

The styles are uneven to short in length (about 0.3 to 0.5 cm), thin to average in caliper, and loosely bunched.

Stigma and style color is near 8D.

Ovaries are usually all enclosed in the calyx.

Hips have not been observed on this variety when grown in Upland, Calif.

FOLIAGE

The compound leaves are usually comprised of 3 to 5 leaflets and are borne abundantly. The 5-leaflet leaves are about 4.9 to 6.3 cm in length and about 3.1 to 4.0 cm in width at the widest point, moderately heavy in texture, and slightly semi-glossy to matte in finish.

The terminal leaflets are about 1.4 to 2.3 cm in length and about 1.1 to 1.8 cm in width at the widest point, shaped oval to ovate with acute apices and rounded bases. Their margins are usually simply serrate.

The upper surface of the mature leaf is between 147A and 139A. The under surface of the mature leaf is between 148C and 139D.

The upper and under surface of the young leaf is between 146B and 137C, sometimes very lightly suffused with near 183C.

The rachis is average in caliper and mostly smooth. The upper side moderately grooved with few hairs and stipitate glands on the edges of the grooves. The under side of the rachis is mostly smooth with few stipitate glands and very few small prickles. The rachis color is between 148C and 139D.

The stipules are about 0.7 to 1.2 cm in length and moderately wide (about 0.3 to 0.5 cm) with somewhat short straight points that usually turn out at an angle of more than 45 degrees and sometimes recurve toward the stem. The stipules color is between 148C and 139D.

The petiole is about 0.6 to 1.1 cm in length and about 0.1 to 0.2 cm in diameter at the widest point. The petiole color is between 148C and 139D.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has a miniature bushy, upright and compact growth habit (about 45 to 62 cm in height and about 30 to 41 cm spread at the widest point), with very full branching.

It displays very vigorous growth and the canes are of good caliper. The color of the major stems is between 147B and 138B. They bear very few medium size prickles that are about 0.3 to 0.4 cm in length.

The prickles are almost straight angled slightly downward with a medium length narrow base; prickle color is near 165B. The major stem bears no small prickles.

The color of the branches is between 146A and 138A. They bear few medium size prickles which are of similar size and shape to the medium size prickles on the major stems; prickle color is near 162D. The branches bear no small prickles.

The color of the new shoots is between 144A and 143C sometimes very lightly suffused with near 183C. They bear few medium prickles which are of similar size and shape to the medium prickles on the major stems; prickle color is near 144C. The shoots bear no small prickles.

I claim:

1. A new and distinct miniature rose plant of the variety substantially as described and illustrated herein.

* * * * *

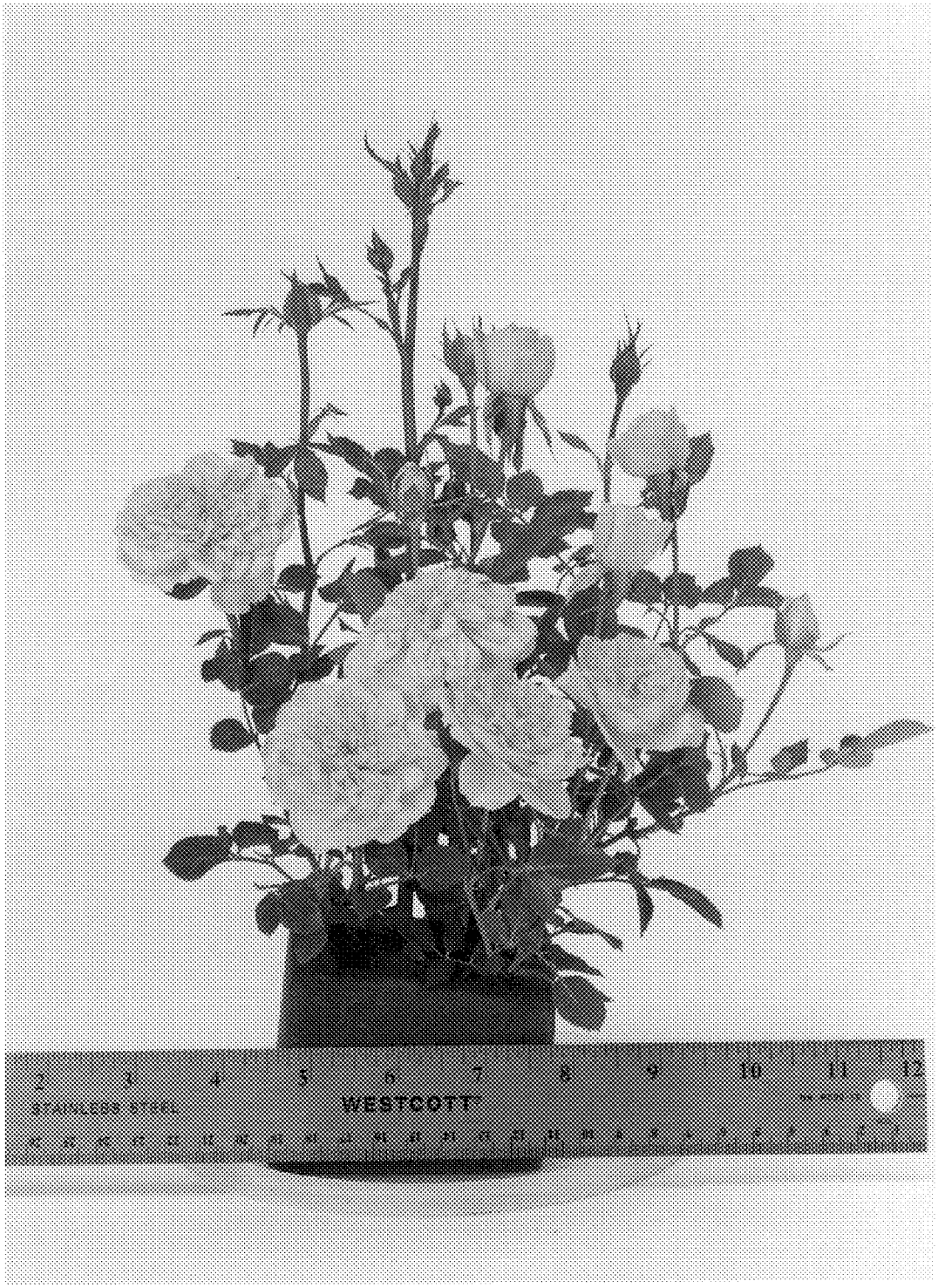
WESTCOTT